(12) United States Patent
Dayton et al.

(10) Patent No.: US 7,713,727 B2
(45) Date of Patent: May 11, 2010

(54) PROCESS FOR IMPROVING ENZYMATIC DEGUMMING OF VEGETABLE OILS AND REDUCING FOULING OF DOWNSTREAM PROCESSING EQUIPMENT

(75) Inventors: Chris L G Dayton, Bourbonnais, IL (US); Kerry P. Staller, Garrett, IN (US); Thomas L Berkshire, Greensbergh, IN (US)

(73) Assignee: Bunge Oils, Inc., Saint Louise, MO (US)

( * ) Notice: Subject to any disclaimer, the term of this patent is extended or adjusted under 35 U.S.C. 154(b) by 43 days.

(21) Appl. No.: 10/556,816

(22) PCT Filed: Dec. 17, 2004

(86) PCT No.: PCT/US2004/042780

§ 371 (c)(1),
(2), (4) Date: Jul. 19, 2006

(87) PCT Pub. No.: WO2005/063950

PCT Pub. Date: Jul. 14, 2005

(65) Prior Publication Data

US 2007/0134777 A1    Jun. 14, 2007

Related U.S. Application Data

(60) Provisional application No. 60/531,192, filed on Dec. 19, 2003.

(51) Int. Cl.
*C12S 3/00* (2006.01)
*C10G 9/16* (2006.01)

(52) U.S. Cl. .................. 435/267; 435/262; 435/271; 208/48 R (58) Field of Classification Search ................. 585/950; 208/47, 48 R; 554/8; 435/262, 267, 271
See application file for complete search history.

(56) References Cited

U.S. PATENT DOCUMENTS 4,154,750 A * 5/1979 Moore et al. ................. 554/190
4,551,226 A * 11/1985 Ferm ..................... 208/48 AA
4,584,141 A * 4/1986 Paulitz et al. ............... 554/190

(Continued)

FOREIGN PATENT DOCUMENTS

EP    0 513 709 B2    11/1992

(Continued)

OTHER PUBLICATIONS

PCT International Search Report; Mailed May 25, 2005.

(Continued)

*Primary Examiner*—Porfirio Nazario Gonzalez
*Assistant Examiner*—Yate' K Cutliff
(74) *Attorney, Agent, or Firm*—Jones Day (57) ABSTRACT

A process controls enzymatic degumming characteristics which cause fouling of post-reactor equipment of industrial scale processing of edible oils. An anti-fouling agent including an organic or mineral acid is added after the reactor and before any post-reactor equipment such as heat exchangers and centrifuges. Typically the anti-fouling agent is added at greater than about 100 ppm of the oil, and typically the pH of the aqueous phase of the oil is between about 3.5 and 4.2.

10 Claims, 5 Drawing Sheets

U.S. PATENT DOCUMENTS

| | | | |
|---|---|---|---|
| 4,698,185 A | | 10/1987 | Dijkstra et al. |
| 5,264,367 A | * | 11/1993 | Aalrust et al. ............... 435/271 |
| 5,696,278 A | | 12/1997 | Segers |
| 6,001,640 A | * | 12/1999 | Loeffler et al. ............... 435/271 |

FOREIGN PATENT DOCUMENTS

EP        0 622 446 A2     11/1994

OTHER PUBLICATIONS

Brumlik et al. *J. Bacterial.* (1996) vol. 178: 2060-2064.

Shu et al. *Biotechnol Lett* (2007) 29:1875-1879.

Maria et al., *Appl. Microbial. Biotechnol.* (2007) 74:290-300.

Clausen, K., *Eur. J. Lipid Technol.*, 103 (2001) 333-340.

Clausen et al. "A New Microbial Phospholipase for Degumming of Vegetable Oil", 93rd AOCS Annual Meeting & Expo, on May 5-8, 2002 at Montréal, Québec, Canada.

Dahlke, et al. *Proceedings of the World Conference on Oilseed and Edible Oils Processing*, 1996, pp. 53-59, "EnzyMax and Alcon—Lurgi's Route to Physical Refining".

* cited by examiner

PROCESS FOR IMPROVING ENZYMATIC DEGUMMING OF VEGETABLE OILS AND REDUCING FOULING OF DOWNSTREAM PROCESSING EQUIPMENT

CROSS REFERENCE TO RELATED APPLICATION

Provisional Patent Application Ser. No. 60/531,192, filed Dec. 19, 2003, incorporated by reference hereinto.

BACKGROUND OF THE INVENTION

1. Field of the Invention

This invention generally relates to processes for improving enzymatic degumming of vegetable oils. The process reduces fouling in post-reaction equipment. The invention is especially suitable for use in production lines within which edible oil is treated to prepare edible oil of salad oil quality. More particularly, the invention relates to process enhancements that create conditions in the oil being processed for minimizing build-up on equipment through which the thus treated oil passes.

2. Description of Related Art

Vegetable-based edible oils long have been processed into salad oils. A principal procedure in such processing is the so-called caustic process. In such a process, crude vegetable oil may or may not be filtered and may or may not be acid or water degummed. The filtration of crude oil is only utilized when "clear and brilliant" food grade lecithin is produced from a water degumming process. Degumming of crude oil with the aid of an acid, burns the lecithin yielding a product that is not desirable. In the water degumming process, crude oil is combined with water and degummed crude is prepared, with gums being removed and collected as desired. Water degumming can remove about two-thirds of the gums present in the crude oil. Typically, phosphoric acid is injected into the degummed crude, followed by sodium hydroxide in order to provide caustic treated oil, with soapstock being removed and collected as desired. Next, silica is added to the caustic treated oil, and spent silica is removed. Bleaching earth then is added to the silica treated oil to provide bleached oil, spent clay being removed. Then water is added to the bleached oil in a deodorizing process, with a distillate being separated. A drawback of such caustic processes is relatively low yields, plus the multiple steps that are followed to achieve desired salad oil quality oil.

The role of phosphoric acid is to treat the lecithin components in the oil. This process includes an add-back neutralization of the phosphoric acid which is needed to neutralize free fatty acids, yielding sodium soaps which separate out. It is recognized that taking an approach different from caustic oil refining could have advantages in the oil processing industry.

Approaches have been proposed whereby edible oil products are processed into salad oil products by an enzymatic approach during which fatty acids remain in the oil rather than following the separation approach of caustic refining, and the fatty acid content is transformed and stays in the vegetable oil until it is separated, such as by centrifugation.

In the oil refining art, references such as Aalrust et al. U.S. Pat. No. 5,264,367, incorporated by reference hereinto, teach enzymatic treatment of edible oils. In such approaches, phosphorus-containing components of an edible vegetable or animal oil that has been wet refined are reduced by enzymatic decomposition by contacting the oil with an aqueous solution of phospholipases A1, A2 or B and then separating the aqueous phase from the treated oil. This is said to reduce the phosphorus level in the oil to a substantial degree. While enzymatic treatment processes show good potential, the present invention achieves improvements over these processes. This invention provides means for improving oil degumming processes.

The present invention provides a novel type of process which facilitates the use of enzymes in edible oil refining, including degumming operations. The invention incorporates a post-reaction addition to reduce fouling. More specifically, anti-fouling component is added promptly downstream of the enzyme reactor. The anti-fouling component imparts enhanced processing properties to the degummed oil.

The art of enzymatic degumming has developed to provide, for example, the ability to hydrate selected cleavage sites of a lecithin or fatty acid natural oil component which needs to be degummed. Those enzymes having an A1 characteristic cleave the A1 site of the triglyceride molecule, enzymes having an A2 characteristic cleave at the A2 or B, or middle site, and those of a C characteristic cleave at the A3 site, which in these types of triglycerides have the undesirable phosphorus atom.

Heretofore, it has not been appreciated that enzymatic degumming operations of this type bring with them an undesirable build-up of residue on blades and other working surfaces of downstream equipment such as heat exchangers and centrifuge equipment. The combination of a post-reactor addition of an anti-fouling component and the enzymatic refining approach result, according to the invention, in high yield and smooth operating industrial-scale edible oil processing plants.

SUMMARY OF THE INVENTION

In accordance with the present invention, processes are provided which have characteristics to improve enzymatic degumming of vegetable oils. These processes have as a principal component the use of an anti-fouling component or additive after the primary degumming reaction, that is after the enzyme and the edible oil are reacted so as to cleave in accordance with the specific characteristics of the enzyme. The preferred anti-fouling additive is a food grade acid.

A general object and aspect of the present invention is to provide a process which improves the operational characteristics to a considerable degree and without substantial variation in an industrial-scale edible oil degumming operations that incorporate very advantageous enzyme reaction approaches.

Another aspect or object of this invention is that it provides degummed edible oils in an efficient manner and reduces down time which is caused by the enzymatic approach that brings yield advantages.

Another aspect or object of this invention is that it provides salad oil quality edible oils through an enzymatic degumming approach while addressing a serious processing issue through significantly reducing fouling in post-reactor processing equipment.

Other aspects, objects and advantages of the present invention, including the various features used in various combinations, will be understood from the following description according to the preferred embodiments of the present invention, taken in conjunction with the drawings in which certain specific features are shown.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

The present invention is directed toward refining of edible oils by a procedure which includes a degumming operation. Production includes cleavage into hydrated sites by an enzyme reaction and subsequent handling of the oil in a manner to control undesired build up which reduces the operational efficiency of downstream equipment.

In enzymatic degumming, heat exchange units and centrifuge equipment downstream of the retention reactor foul quickly with released calcium and magnesium salts or soaps. The natural pH of the enzymatic reaction contributes to the rapid fouling. By injecting a relatively small amount of anti-fouling component after the reactor and before downstream equipment, for example in the heat exchangers, fouling is eliminated or, at least, very significantly reduced.

Enzymatic degumming of vegetable oil with certain versions of phospholipase A-1 requires a reaction pH of between 4.0 and 5.0. Optimum pH for this reaction is between 4.5 and 5.0. However, in the optimum pH range, calcium and/or magnesium released during the enzymatic reaction combine with the buffering or chelating acids used to control the reaction conditions, typically leading to salt formation and fouling of equipment coming into contact with same.

Without benefit of the present invention, the combined calcium and magnesium salts would precipitate on hot surfaces such as heat exchangers and centrifuge disk stacks. For the heat exchangers, if this fouling were not prevented, several hours of washing with a strong hot solution of acid would be required to clear up the deposits. For the centrifuge, the buildup would have to be removed manually by disassembling the unit and physically scraping each disk. The cleaning process for the centrifuge typically can require 40 worker-hours to complete.

It can be appreciated that the fouling can be much less if the reaction is run closer to pH 4.0. However, this brings with it the considerable disadvantage that the rate of reaction is slower at lower pH levels. Furthermore, it is difficult to keep the pH from slipping below 4.0 in such situations, in which event the reaction stops completely. Thus, a straightforward addition of acidic media to lower pH levels has serious production issues.

The invention allows for the enzymatic reaction to be run at its optimum pH for performance, in most instances between 4.5 and 5.0 pH. After exit from the enzyme degumming reactor, the anti-fouling agent is added, such addition being shortly before flow of oil to post-reactor equipment. Post-reactor injection of the anti-fouling agent or component provides an enzyme degummed oil and agent mixture having a pH that is dropped to a lower level after the degumming reaction is complete. This level has been found to be a non-fouling level.

With regard to the anti-fouling agent or component, same preferably is an organic or mineral acid which is suitable for use in food processing. The acids should lower the pH to 4.5 or below and may act as a metal chelator. Examples include citric acid, maleic acid, malic acid, phosphoric acid, and so forth.

An organic or mineral acid compatible with the vegetable oil and having a pKa less than 4.0 is preferred. This anti-fouling agent or component is injected into the line and leaves the enzymatic reactor before the mixture enters the heat exchanger(s) and/or centrifuge(s) or other downstream equipment.

Flow is controlled to be proportional to the oil flow and to bring the aqueous phase of the mixture downstream of the reactor to a pH between about 2 and 4.5 preferably between about 3.5 and 4.2, most preferably between about 3.8 and about 4.0. In many instances, maintaining the aqueous phase at about 4.0 pH is a very suitable target. Lower pH numbers will also achieve the desired effect, but are wasteful of acid and downstream neutralizing agents.

Concerning the anti-fouling agent, it is preferred to use citric acid to control the pH in the flow from the enzyme degumming reactor. Such an acid is advantageous for this purpose and often is readily available in industrial-scale oil processing plants. Other vegetable-oil compatible acids such as phosphoric acid, malic acid or maleic acid could also be used, depending on cost and availability. The acid must be sufficiently strong to lower the pH of the mixture aqueous phase to below 4.5, typically at 4.0 or just below, but not damage the oil by reactive or oxidative attack.

Referring to the enzyme activity which can proceed within the reactor, a phospholipase mode of action at different cleavage sites can be summarized as follows:

The X substituent can be any of hydrogen, choline, ethanolamine, serine, inositol, and the like.

An enzyme mode of action for lecithin is shown in the following reaction sequence.

This illustrates a general enzyme mode of action which is typical of the enzyme reaction processes with respect to which the present invention is practiced. This particular illustration shows an enzyme reaction of lecithin into lyso-lecithin and free fatty acid.

Structures of lipids, namely lecithin and fats in general, can be shown as follows, wherein each of $R^1$, $R^2$ and $R^3$ etc. represent different fatty acid chains, and wherein X represents hydrogen, choline, ethanolamine, serine, inositol, and the like. Reaction sites are available in these structures.

Figure 1:
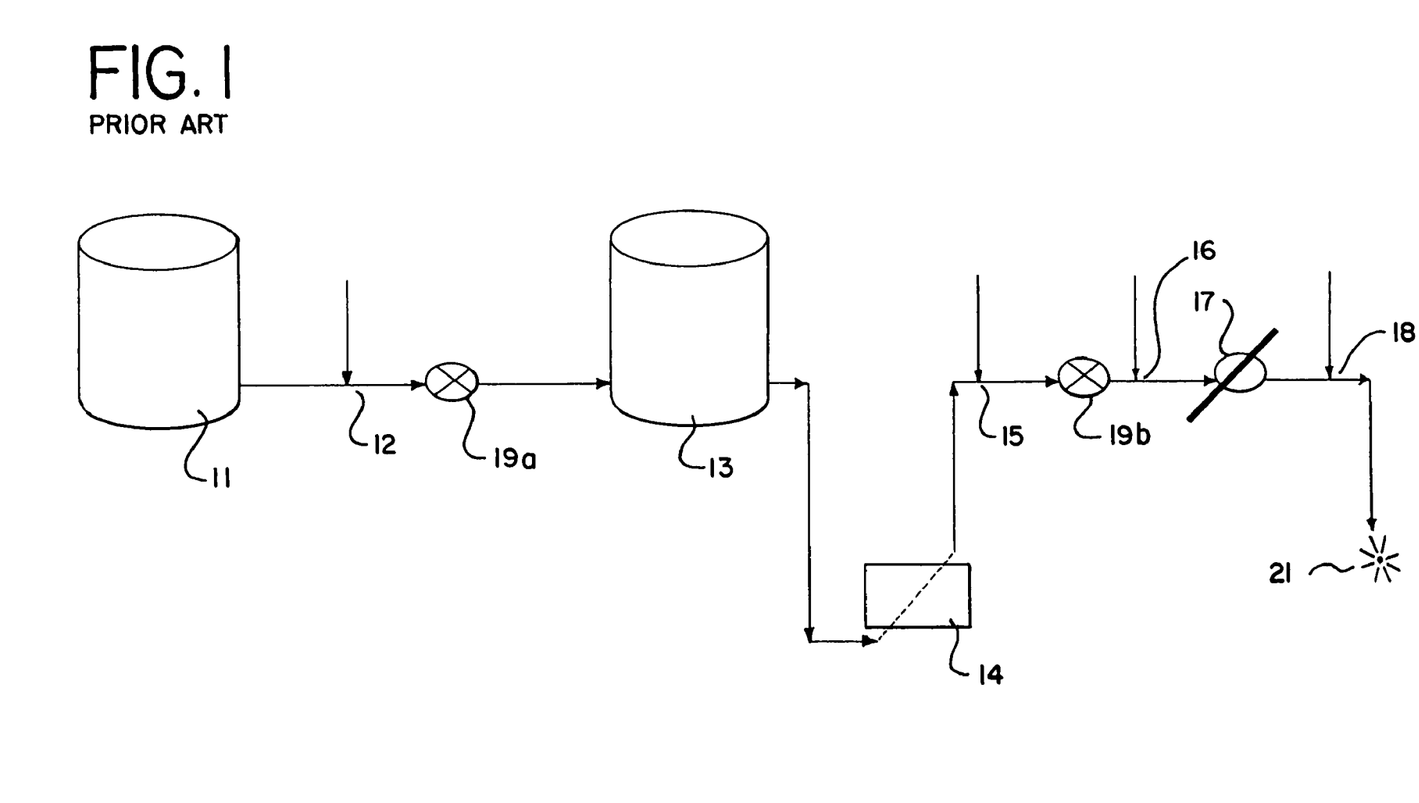
FIG. 1 is a schematic illustration of an overall processing sequence according to the prior art, beginning with the edible oil in the reaction chamber or hold tank.

A typical prior art enzyme reaction sequence is shown in FIG. 1. A supply of degummed oil is represented by vessel 11. An agent such as citric acid is introduced at 12, and the flow continues through an intensive mixer 19a such as a model MX-90 of Alpha Laval. This then flows to an acid retention location 13. Flow then is to a heat exchanger 14, known in the industry as an "economizer". Caustic addition is shown at introducer 15, followed by flow through another intensive mixer 19b. Water can be added at 16 before flowing into a cooler 17 to provide heat exchange action. Enzyme addition is shown at 18 for degumming the oil with the assistance of disperser 21. The disperser can be a multi-stage in-line disperser Dispax™ Reactor, available from IKA. In this prior art approach, the acid (typically an organic acid) introduced at 12 and the caustic (typically sodium hydroxide) introduced at 15 make up a buffer solution at a pH of 4.5 to 5.2. This buffered pH range is valuable to achieve optimum enzyme performance when same is added at 18. Typically the caustic is added at about 1.5 molar equivalents of the added acid.

Figure 2:
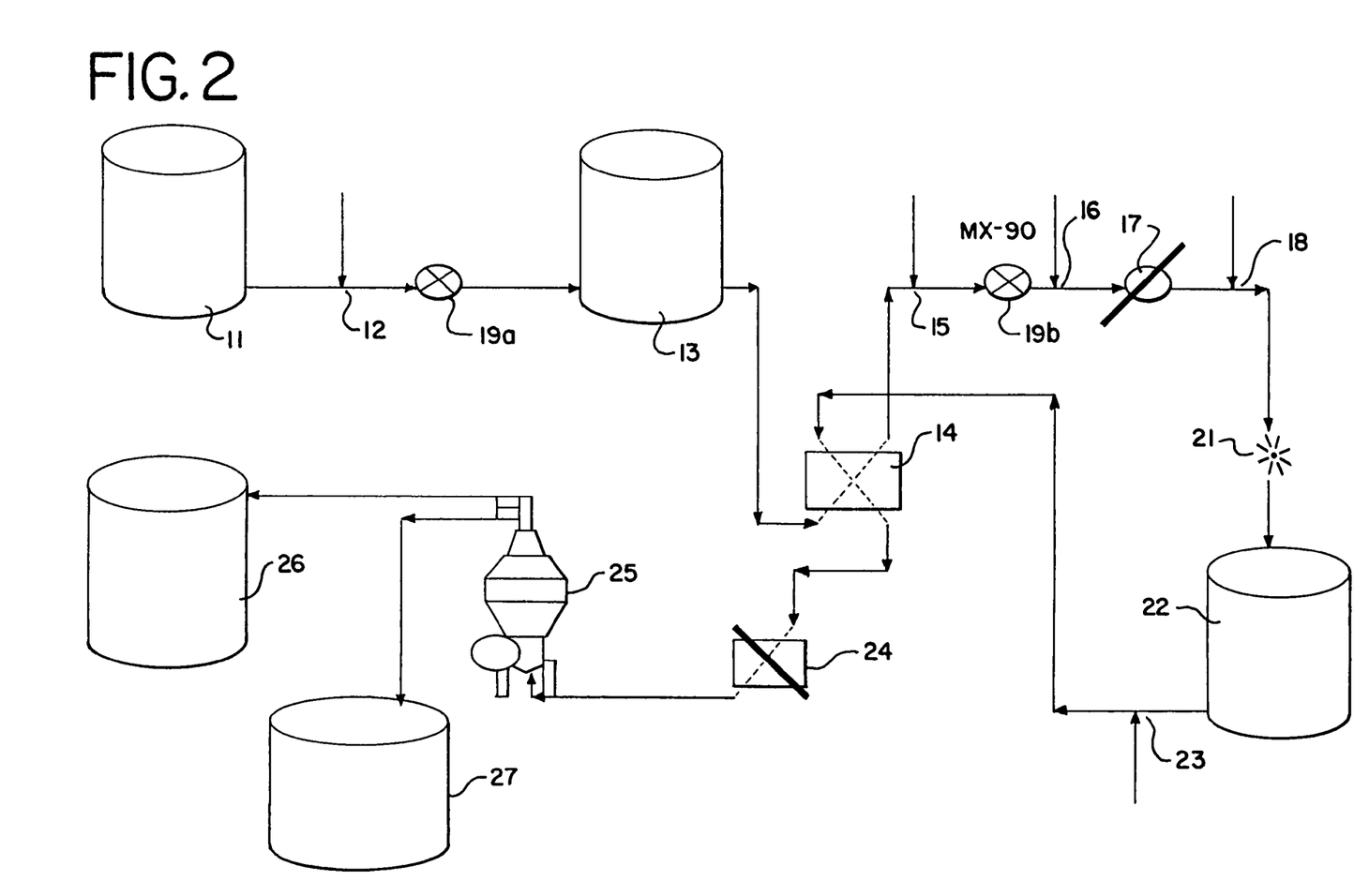
FIG. 2. is a flow chart of a typical industrial-scale process which follows the present invention
Figure 3:
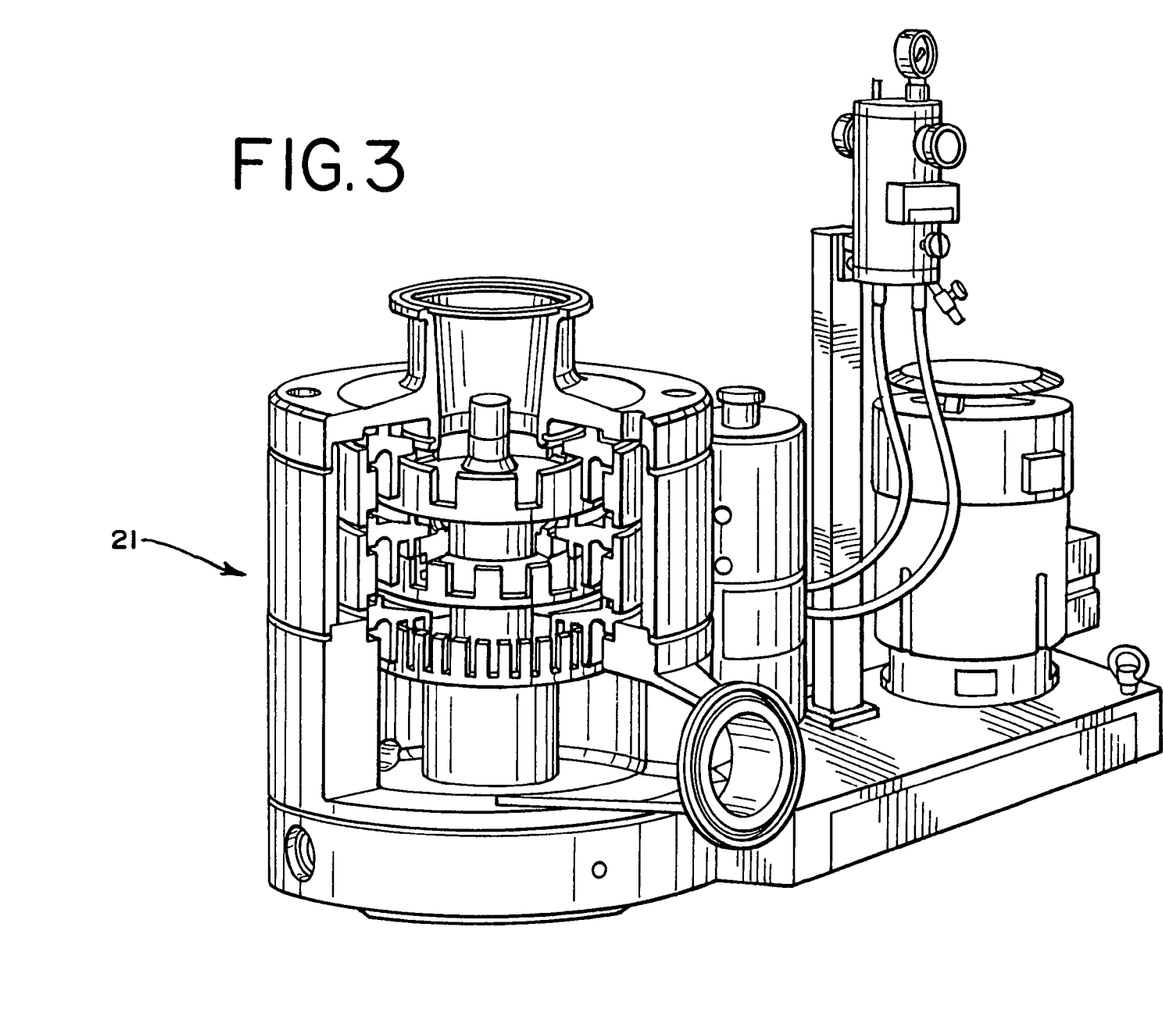
FIG. 3 is a perspective view, partially cut away, of a high shear reactor which is especially suitable for reacting enzyme with the edible oil in a very efficient and advantageous manner.
Figure 4:
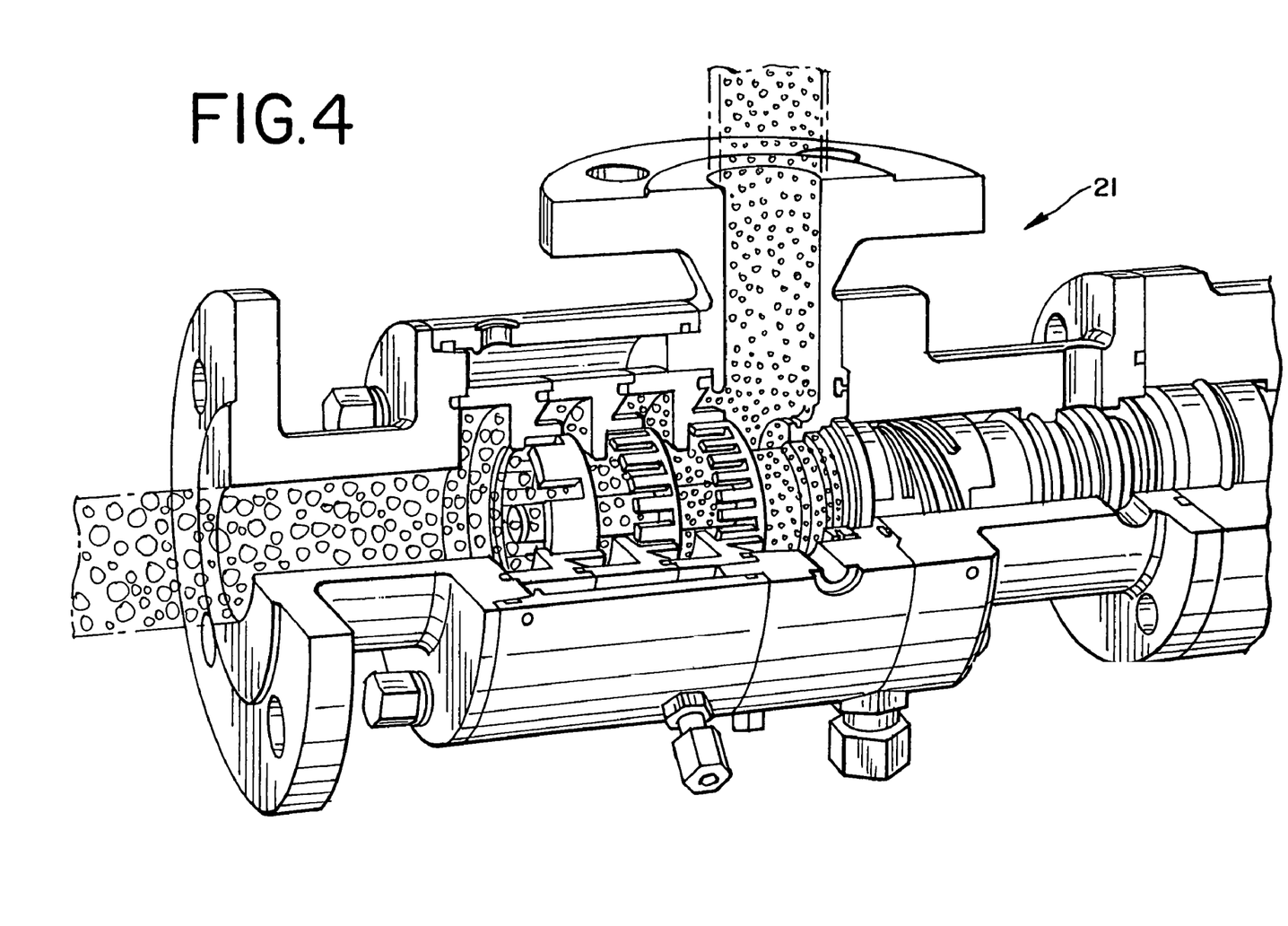
FIG. 4 is a perspective view, partially cut away, of an operational mixing device and approach which can be preferred for use in the process, showing flow interaction and operational details.

FIG. 2 illustrates a processing incorporating line a preferred embodiment of the present invention. The description above concerning FIG. 1 is applicable to the FIG. 2 details through the flow into the disperser 21. A typical disperser such a Dispax™ Reactor of IKA is illustrated in FIG. 3 and FIG. 4. Preferred dispersers are powerful high mechanical shear mixers, such as an IKA works 100 horsepower Dispax™ Reactor. Such produces a very stable mechanical emulsion and no emulsifiers are required due to the high mechanical shear force utilized. The emulsion allows the enzyme to react with the phospholipids, transforming them into water-soluble lyso-phospholipids. After such disperser flow, enzyme and oil can be within a tank 22, which can be called a retention tank or a reaction tank.

In keeping with the invention, an anti-fouling agent or component is added at 23 by a suitable injection mechanism. This addition lowers the pH to below 4.5 as discussed elsewhere herein, such lowering being before the oil flow reaches downstream equipment, typically one or more heat exchangers, centrifuges and other oil processing equipment. In the illustrated preferred embodiment, the lowered pH condition is present as the oil flows through heat exchanger or economizer 14, through a preheater 24, and into and through a centrifuge 25. It is believed that at least the economizer and the preheater assist in mixing and/or dispersing the anti-fouling agent into the oil. The flow out of the downstream centrifuge will be the refined vegetable oil surge 26 through one channel, which is separated from soapstock and/or secondary gums 27.

Without this aspect of adding the anti-fouling agent at such location upstream of the heat exchangers and centrifuge, fouling of these post-reaction components had been experienced. Such fouling resulted in dramatic increases in back pressure within these components. Experience with this condition has been so severe that the centrifuge or centrifuges would begin to become unbalanced, causing vibration. Experience also indicates that adding anti-fouling agent or component before the centrifuge location but after the heat exchangers, such as the preheater and economizer, did not provide a solution to the fouling problem. Instead, the centrifuge and the plate and frame heat exchangers experienced unacceptable fouling.

It also has been determined that the effectiveness of the anti-fouling agent or component addition will vary with the concentration of this agent or component. Typically, the anti-fouling agent concentration should be at least 100 ppm. A value as high as 300 ppm works well, but is not as cost effective as lower levels. A reasonable working range is between about 100 ppm and about 200 ppm, a preferred range being between about 125 ppm and about 175 ppm. Between about 140 ppm and about 160 ppm is especially preferred for effectiveness and cost considerations.

Another component in achieving an anti-fouling effect is the length of time that the anti-fouling agent is in the oil before this oil flow reaches the centrifuge. Traversing this flow path section should be completed in not longer than about one minute, preferably not longer than about 45 seconds, most preferably not longer than about 30 seconds.

Anti-fouling agent addition typically is carried out with a pump. Preferably flow from the pump combines with continuous oil flow to add correct concentrations of the anti-fouling agent so the needed pH drop occurs to a range where potential fouling components are soluble. For example, when citric acid is the anti-fouling agent, calcium and magnesium citrates remain soluble.

It has been found that the present invention will be beneficial irrespective of the specific enzyme used in the operation. Phospholipases can be used, including A-1, A-2, B, C and D. The amount of enzyme will depend on the concentration of the enzyme as it is supplied from its manufacturer, as well as the activity of the enzyme. A typical maximum amount would be about 1% by weight. The concentration of enzyme is primarily a function of the enzyme and the oil and is not particularly relevant to action of the anti-fouling agent and process.

Figure 5:
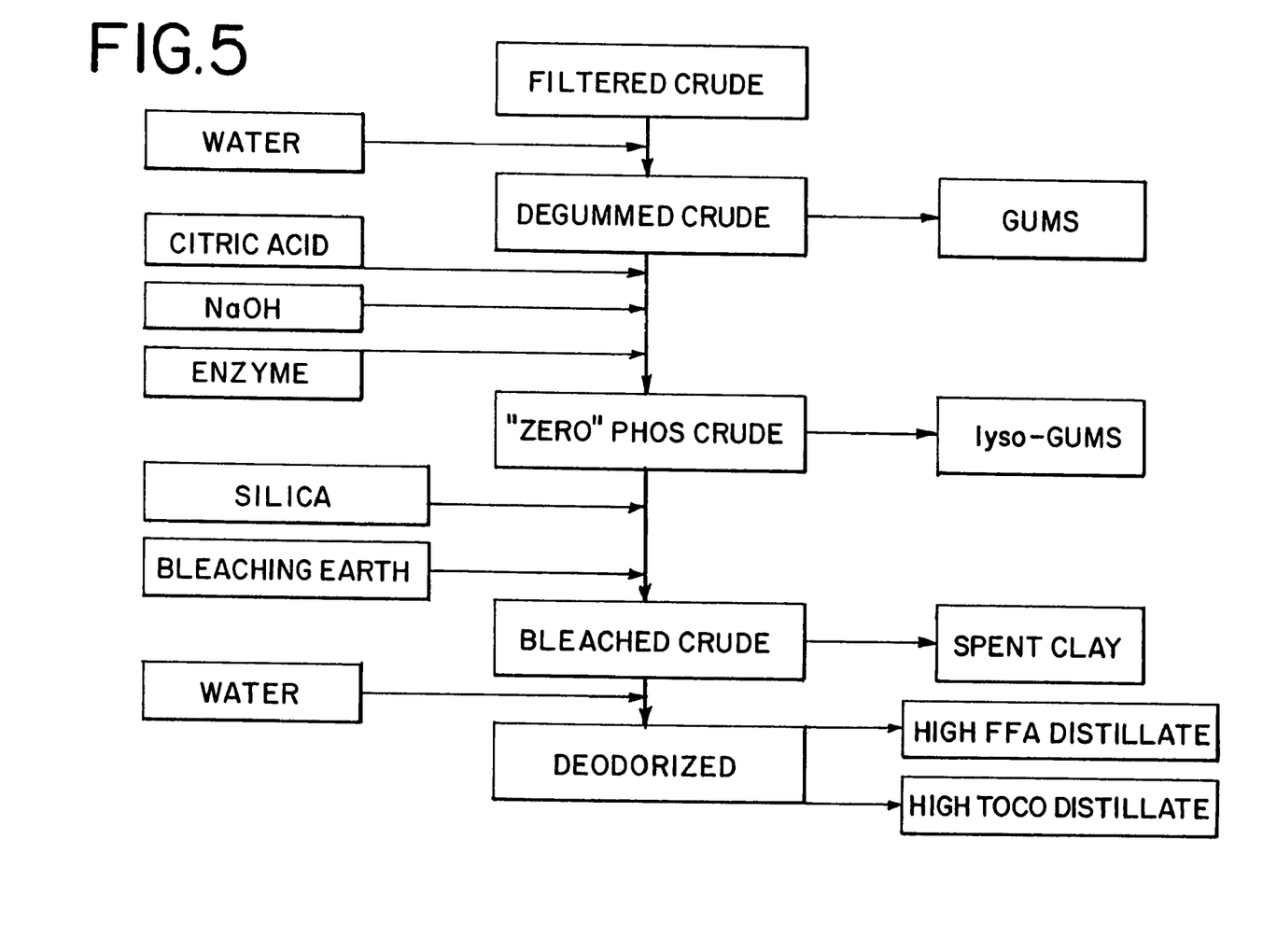
FIG. 5 is a schematic illustration of a processing sequence suitable for incorporating the invention.

An overall flow chart for a process according to the invention is found in FIG. 5. With the present invention, enzyme typically is dosed at a level on the order of between about 20 ppm and about 60 ppm using a high shear mixer, such as shown in the drawings, to mix the enzyme with the oil. The oil then is kept at a temperature of about 45 C. A low water content of only 2 percent is all that is required of the oil being processed by this physical processing approach. This reduces drying costs.

By the use of the anti-fouling agent or component in accordance with the invention, the pH is kept advantageously low. This prevents calcium citrates from forming and precipitating out. Such calcium citrate deposits and other possible formed salts will form undesirable deposits downstream. For example, citrate deposits will otherwise form on working components of downstream equipment.

The finished oil has a phosphorus content which typically is below 2 ppm. After this enzymatic degumming and physical refining, the oil has a phosphorus content of no more than between about 2 and about 5 ppm. In comparison, chemical refining by the caustic process noted above leaves a phosphorus content on the order of no lower than 8 to 10 ppm. Thus the process practiced with the aid of the present invention has the advantage of requiring less silica, such typically being incorporated in order to adsorb the phosphorus remaining after degumming.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A process for reducing fouling of industrial scale edible oil processing equipment, comprising:
   reacting a crude vegetable oil source of edible vegetable oil with an enzyme thereby cleaving fat components of the crude vegetable oil source to provide cleaved and hydrated sites of the phospholipid to provide a reacted edible oil that is an enzymatically treated edible oil;
   thereafter adding a post-reaction anti-fouling component to the reacted edible oil that has been enzymatically treated to solubilize calcium or magnesium citrate salt released during enzymatic reaction on said crude vegetable oil to provide a post-reaction mixture thereof wherein said anti-fouling component is an organic or mineral acid suitable for use with food for human consumption added in an amount between 100 ppm and 300 ppm and reduces the pH of said reacted edible oil's aqueous phase to not greater than 4.5 pH;
   passing a flow of said post-reaction mixture of reacted edible oil and anti-fouling component into and through post-reaction equipment; and
   thereby reducing or preventing calcium or magnesium citrate salt precipitate fouling on working surfaces of the post-reaction equipment through the action of said anti-fouling component present within said reacted edible oil of the post-reaction mixture while same is within the post-reaction equipment.

2. The process in accordance with claim 1, wherein said anti-fouling component is citric acid, phosphoric acid, maleic acid or malic acid.

3. The process in accordance with claim 1, wherein said reacted edible oil's aqueous phase is reduced to between about 3.5 and 4.2 pH.

4. The process in accordance with claim 1, wherein said reacting is characterized by shear mixing.

5. The process in accordance with claim 1, wherein said passing into the downstream processing equipment is completed in nor more than one minute after said adding of anti-fouling component.

6. The process in accordance with claim 1, wherein said enzyme of the reacting step is selected from the group consisting of phospholipase A-1, A-2, B, C and D.

7. The process in accordance with claim 1, wherein said passing into the downstream processing equipment is completed in not more than 45 seconds after said adding of anti-fouling component.

8. The process in accordance with claim 1, wherein said post-reaction equipment comprises centrifuging, heat exchange, economizer or preheated equipment, or blades, channels or other working surfaces of post-reaction equipment.

9. The process in accordance with claim 1, wherein said degummed oil has a residual phosphorus content of not greater than about 5 ppm.

10. The process in accordance with claim 1, wherein said degummed oil has a residual phosphorus content of not greater than about 2 ppm.

* * * * *